(12) United States Patent
Davies et al.

(10) Patent No.: US 9,180,253 B2
(45) Date of Patent: Nov. 10, 2015

(54) MEDICATED MODULE FOR ADMINISTERING FIXED DOSE

(75) Inventors: James Alexander Davies, Warwickshire (GB); Paul Richard Draper, Worcestershire (GB); Steven Wimpenny, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 368 days.

(21) Appl. No.: 13/882,702

(22) PCT Filed: Oct. 31, 2011

(86) PCT No.: PCT/EP2011/069106
§ 371 (c)(1),
(2), (4) Date: Apr. 30, 2013

(87) PCT Pub. No.: WO2012/059457
PCT Pub. Date: May 10, 2012

(65) Prior Publication Data
US 2013/0218089 A1 Aug. 22, 2013

Related U.S. Application Data

(60) Provisional application No. 61/432,704, filed on Jan. 14, 2011.

(30) Foreign Application Priority Data

Nov. 3, 2010 (EP) .................................... 10189797

(51) Int. Cl.
*A61M 5/28* (2006.01)
*A61M 5/24* (2006.01)
*A61M 5/20* (2006.01)
*A61M 5/32* (2006.01)
(Continued)

(52) U.S. Cl.
CPC ............. *A61M 5/283* (2013.01); *A61M 5/2066* (2013.01); *A61M 5/2425* (2013.01); *A61M 5/2448* (2013.01); *A61M 5/3294* (2013.01);
(Continued)

(58) Field of Classification Search
CPC .............. A61M 2005/3247; A61M 2005/3267
See application file for complete search history.

(56) References Cited

U.S. PATENT DOCUMENTS 3,892,237 A * 7/1975 Steiner .......................... 604/200
5,637,087 A * 6/1997 O'Neil et al. ................... 604/82
(Continued)

FOREIGN PATENT DOCUMENTS

GB       2206800 A      1/1989

OTHER PUBLICATIONS

Form PCT/IB/373, International Preliminary Report on Patentability.

*Primary Examiner* — Nicholas Lucchesi
*Assistant Examiner* — Melissa A Snyder
(74) *Attorney, Agent, or Firm* — McDonnell Boehnen Hulbert & Berghoff (57) ABSTRACT

A medicated module attachable to a drug delivery device. The medicated module comprises a housing configured for attachment to a drug delivery device. The drug delivery device comprises a first medicament. A collapsible reservoir is contained within the housing. A pre-determined volume of a second medicament is contained within the reservoir. A needle arrangement is configured within the housing and the needle arrangement is arranged in fluid communication with the collapsible reservoir. A needle shroud may be configured, such that, during an injection step, the shroud acts on the reservoir to inject the second medicament.

15 Claims, 5 Drawing Sheets

(51) Int. Cl.
*A61M 5/178* (2006.01)
*A61M 5/315* (2006.01)

(52) U.S. Cl.
CPC ............ *A61M5/2033* (2013.01); *A61M 5/2466* (2013.01); *A61M 5/326* (2013.01); *A61M 2005/1787* (2013.01); *A61M 2005/247* (2013.01); *A61M 2005/31516* (2013.01); *A61M 2005/3247* (2013.01); *A61M 2005/3267* (2013.01)

(56) References Cited

U.S. PATENT DOCUMENTS

| | | | |
|---|---|---|---|
| 6,562,002 | B1 | 5/2003 | Taylor |
| 6,723,074 | B1 * | 4/2004 | Halseth ........................ 604/201 |
| 2006/0229562 | A1 | 10/2006 | Marsh et al. |
| 2006/0276755 | A1 | 12/2006 | Sullivan et al. |
| 2007/0191780 | A1 | 8/2007 | Modi |
| 2010/0100047 | A1 | 4/2010 | Glejbol et al. |

\* cited by examiner

MEDICATED MODULE FOR ADMINISTERING FIXED DOSE

CROSS REFERENCE TO RELATED APPLICATIONS

The present application is a U.S. National Phase Application pursuant to 35 U.S.C. §371 of International Application No. PCT/EP2011/069106 filed Oct. 31, 2011, which claims priority to European Patent Application No. 10189797.3 filed Nov. 3, 2010 and U.S. Patent Application No. 61/432,704 filed Jan. 14, 2011. The entire disclosure contents of these applications are herewith incorporated by reference into the present application.

FIELD OF INVENTION

The present application relates to medical devices and methods of delivering at least two drug agents from separate reservoirs using devices having only a single dose setter and a single dispense interface. A delivery procedure initiated by the user causes a non-user settable dose (i.e., a fixed dose) of a second drug agent along with a variable set dose of a first drug agent to be delivered to the patient. The drug agents may be available in two or more reservoirs, containers, or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. This invention is of particular benefit where combination therapy is desirable, but not possible in a single formulation for reasons such as, but not limited to, stability, compromised therapeutic performance, and/or toxicology.

For example, in some cases it might be beneficial to treat a person suffering from diabetes with a combination of a long acting insulin along with a glucagon-like peptide-1 (GLP-1). This GLP-1 is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

A number of potential problems can arise when delivering two active medicaments or "agents" simultaneously. As just one example, the two active agents may interact with each other during the long-term, shelf life storage of the formulation. Therefore, there are certain advantages to storing the active components separately and then potentially combine them at the point of delivery, e.g. injection, needle-less injection, pumps, or inhalation. However, any potential process for combining the two or more agents needs to be straight forward and convenient for the user to perform reliably, repeatedly, and safely.

One further concern is that the quantities and/or proportions of each active agent making up the potential combination dose or therapy may need to be varied for each user or at different stages of their therapy. Again, as just one example, one or more active agents may require a titration period to gradually introduce a patient to a "maintenance" dose. A further example would be if one active agent requires a non-adjustable fixed dose while the other agent is varied in response to a patient's symptoms or physical condition. This potential concern could mean that pre-mixed formulations of multiple active agents may not be suitable as these pre-mixed formulations would have a fixed ratio of the active components, which could not be varied by the healthcare professional or user.

Additional concerns may arise where a multi-drug compound therapy is required, because certain users may not be able to cope with having to use more than one drug delivery system or make the necessary accurate calculation of the required dose combination. This is especially true for users with dexterity or computational difficulties.

Accordingly, there exists a strong need to provide devices and methods for the delivery of two or more medicaments in a single injection or delivery step that is simple and safe for the user to perform and that also tends to reduce a patient's anxiety towards injections and/or needles.

SUMMARY

The present application discloses a medicated module attachable to a drug delivery device. The medicated module comprises a housing configured for attachment to a drug delivery device that comprises a first medicament. A collapsible reservoir is contained within the housing. A pre-determined volume of a second medicament is contained within the reservoir. A needle arrangement is configured within the housing and the needle arrangement is arranged in fluid communication with the collapsible reservoir. A needle shroud may be configured, such that, during dispense, the shroud acts on the collapsible reservoir. For example, the needle shroud is configured, such that, during an injection step, the shroud acts on the collapsible reservoir.

A medicated module according to the present invention may be attachable to a drug delivery device. One example of a drug delivery device that may be used with the medicated module may be in the form of a pen type drug delivery device that may contain a cartridge or other reservoir of medication. This cartridge may be cylindrical in shape and may be manufactured in glass. The cartridge may be sealed at one end with a rubber bung and at the other end by a rubber septum. The drug delivery device may be designed to deliver multiple injections. The delivery mechanism may be powered by a manual action of the user. However, the injection mechanism may also be powered by other means such as a spring, compressed gas or electrical energy. A drug delivery device may be an injection pen comprising at least one of the above listed features. A drug delivery device may also comprise a syringe, preferably a prefilled syringe.

In a preferred embodiment a master drug compound, such as insulin, contained within a multiple dose, user-selectable device could be used with a single use, user-replaceable, module that contains a single dose of a secondary medicament and the single dispense interface. When connected to the drug delivery device the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In another embodiment, a drug delivery system to deliver two or more medicaments operable through a single dose setter and a single dispense interface is provided. The drug delivery system includes a housing containing a single dose setter operably connected to a primary reservoir of medicament containing at least one drug agent and a dose button operably connected to the primary reservoir of medicament. The drug delivery system further includes a medicated module configured for fluid communication with the primary reservoir. The medicated module comprises a proximal end and a distal end, where the proximal end has a connector configured for attachment to the housing. The medicated module further includes a collapsible reservoir containing a secondary medicament and an output needle. Still further, the medicated module includes a shroud, capable of axial displacement. In accordance with one embodiment, a single activation of the dose button of the drug delivery device causes the second medicament from the collapsible reservoir and the first medicament from the primary reservoir to be expelled through the output needle.

A further independent aspect of the invention relates to a medicated module for use with a drug delivery device, said medicated module comprising:

a housing configured for attachment to said drug delivery device, said drug delivery device comprising a first medicament, a collapsible reservoir contained within said housing, a pre-determined volume of a second medicament contained within said collapsible reservoir, a needle arrangement configured within said housing, said needle arrangement arranged in fluid communication with said collapsible reservoir and said drug delivery device, and a needle shroud configured partially within said housing, wherein, said needle shroud is configured to compress said collapsible reservoir to dispense said second medicament through said needle arrangement.

In one embodiment the medicated module according to this disclosure, is configured such that, during dispense, said second medicament is dispensed before a first dose of said first medicament contained within said drug delivery device.

In one embodiment the first dose of said first medicament contained within said drug delivery device comprises a fixed dose. In another embodiment the first dose of said first medicament comprises a variable dose.

In a further embodiment of the medicated module according to this disclosure the pre-determined volume of said second medicament contained within said collapsible reservoir comprises a fixed dose of said second medicament.

In one embodiment the medicated module according to this disclose comprises a housing, wherein said housing is configured for permanent attachment to said drug delivery device.

In one embodiment the medicated module according to this disclose comprises a shroud, wherein said shroud is biased within said housing. In a further embodiment the shroud may be biased within said housing by a spring.

In one embodiment the medicated module according to this disclose comprises a shroud, wherein a portion of said shroud comprises a tubular shape so that said tubular shape substantially conceals a portion of said needle arrangement.

In a further embodiment the shroud may be axially moveable relative to said housing.

In another embodiment the medicated module according to this disclosure comprises a needle arrangement, wherein said needle arrangement comprises a first needle in fluid communication with said collapsible reservoir and a second needle in fluid communication with both said first medicament contained within said drug delivery device and said collapsible reservoir.

In another embodiment the medicated module according to this disclosure may comprise a needle arrangement, wherein said needle arrangement comprises a single unitary needle configured to be in fluid communication with both the first and second medicaments. The single unitary needle may extend through a flexible reservoir. The single unitary needle may comprise a proximal piercing end configured for fluid communication with the drug delivery device. The single unitary needle may comprise a distal piercing end configured for injection. The single unitary needle may comprise at least one side-cored hole located inside said collapsible reservoir; wherein the at least one hole is arranged to facilitate the flow of medicament from the collapsible reservoir on retraction of the needle shroud into the needle. When the shroud is retracted the sealed reservoir may be compressed and the medicament from said reservoir may be pushed through said at least one side cored hole into the needle. In a preferred embodiment, the at least one side-cored hole may be located just below the top member or the proximal end of the collapsible reservoir. Hence, when the shroud is retracted the sealed reservoir may be pushed to slide up along the needle and the medicament from said reservoir may be pushed through said at least one side cored hole into the needle. An embodiment like this may be potentially easier to manufacture and assemble as the needle can be fixed to the top side of the collapsible reservoir and only needs to be slidably sealed to the bottom face of the collapsible reservoir such that on refraction of the shroud the sealed reservoir slides up along the needle and expels the fixed dose.

In another embodiment the medicated module according to this disclosure comprises a second medicament, wherein said second medicament comprises a GLP-1 or GLP-1 analog.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 2:
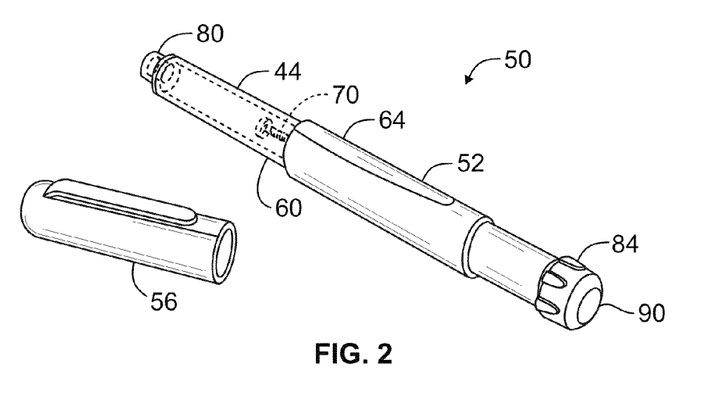
FIG. 2 illustrates one possible drug delivery device that can be used with Applicants' proposed medicated module arrangements to deliver the predefined therapeutic profile illustrated in FIG. 1.

The presently proposed medicated module may be used with a drug delivery device, such as the device illustrated in FIG. 2. In one arrangement, the presently proposed medicated module administers a potentially variable dose of a first medicament and a fixed predetermined dose of a second medicament through a single output or drug dispense interface such as a double ended needle. Setting the dose of the first medicament is done by the user. The volume and size of the second medicament is independently controlled and therefore not influenced by the size of the user selectable dose. This fixed dose of the second medicament contained within the medicated module may be a single dose. The present application is also generally directed to administering a primary dose of a potentially variable dose of a first medicament through the same single dispense interface.

In a preferred arrangement, the drug dispense interface comprises a needle cannula (hollow needle) that can be substantially concealed by a needle shroud. The needle shroud is designed so as to allow a user to administer a first dose that includes a potentially variable dose of a first medicament contained within a drug delivery device and the fixed predetermined dose (i.e., non-user-settable dose) of the second medicament. In one alternative arrangement, the needle shroud may lock out (reversibly or non-reversibly) in a distal position after a user has inserted the needle into the skin. Therefore, substantially all of the volume of second medicament within the collapsible container may be dispensed, and then the needle may be removed from the injection site. This insertion is also normally accompanied by dispense of the user variable and user administered first medicament within the drug delivery device.

The delivery of combination drug products (i.e., a single dose that is made up from the combination of two or more individual drug formulations) in a format where the delivered therapeutic dose profile is predetermined, offers a number of benefits for both a patient and the treatment of a particular condition.

Figure 1:
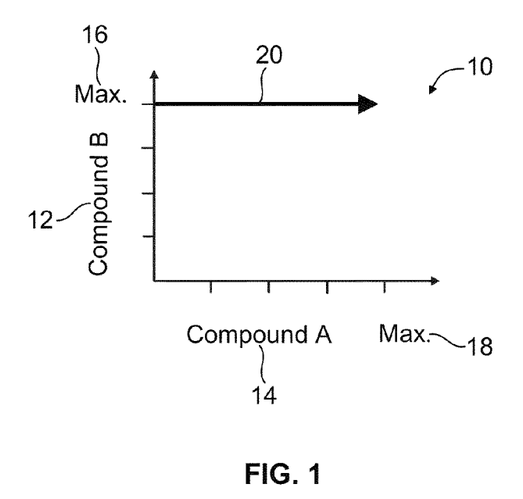
FIG. 1 illustrates a predefined therapeutic profile of one preferred arrangement of Applicants' medicated module for delivering a fixed dose of a second medicament.

For example, one such predefined therapeutic dose profile 10 is illustrated in FIG. 1. This therapeutic profile 10 defines a combination dose 20 that comprises at least two medicaments: Compound A 14 and Compound B 12. Such a therapeutic profile 10 may be referred to as a "fixed dose, user variable dose" profile. That is, such a profile 10 describes a drug delivery system that can deliver a fixed dose of one medicament (i.e., Compound B 12) while also delivering a user selectable dose of another medicament (i.e., Compound A 14), to a single injection site. As represented by this profile 10, the variable Compound A 14 is provided along the x-axis and the constant or fixed Compound B 12 is provided along the y-axis. As illustrated, the combination dose 20 will comprise a maximum dose 16 of Compound B and a variable dose 18 of Compound A. In one arrangement, the variable Compound A 14 is provided in a cartridge of a drug delivery device. This cartridge may be either a replaceable or non-replaceable cartridge. The fixed Compound B 12 may be provided in a medicated module, such as the medicated module 100 illustrated in FIG. 3.

For some drug combinations for which such a "fixed dose, user variable dose" profile 10 is desirable, it may additionally be desirable for the two medicaments to be delivered in a sequential manner. That is, for certain therapeutic regimens, it may be preferable to first deliver a dose of one medicament and then deliver a dose of the other medicament (i.e., one after the other, with minimal or no opportunity for mixing of the two medicaments within the device). Furthermore, it may be preferable for the ullage volume (i.e., the undispensed volume or space in a medicament container) in the medicated module (post injection or medicament dispense) to be smaller than the volume of the fixed dose medicament contained within the medicated module prior to dispense.

One example of a drug delivery device 50 that may be used with the medicated module 100 is illustrated in FIG. 2. In FIG. 2, there is shown a drug delivery device 50 in the form of a pen type drug delivery device that contains a cartridge or other reservoir of medication. This cartridge is typically cylindrical in shape and is usually manufactured in glass. The cartridge is sealed at one end with a rubber bung and at the other end by a rubber septum. The drug delivery device is designed to deliver multiple injections. The delivery mechanism is typically powered by a manual action of the user as described above; however, the injection mechanism may also be powered by other means such as a spring, compressed gas or electrical energy.

More specifically, the drug delivery device 50 comprises a dose setting mechanism 52, a cartridge holder 44, and a removable cap 56. A proximal end 60 of the cartridge holder 44 and a distal end 64 of the dose setting mechanism 52 are secured together. The dose setting mechanism 52 comprises a piston rod 70, such as a threaded piston rod that rotates when a dose is injected.

A connector 80 is provided at a distal end of the cartridge holder 54. This coupling mechanism may be used to connect applicants' medicated module. Any known attachment means can be used to couple the medicated module to this cartridge holder 54, including permanent and removable connection means. Threads, snap locks, snap fits, luer locks, bayonet, snap rings, keyed slots, and combinations of such connections can be used to attach medicated module 100 to drug delivery device 50. As just one example, connector 80 may comprise screw threads. In certain applications, the connector 80 may comprise an exclusive attachment where such an exclusive attachment would only allow such a medicated module to be attached to only certain drug delivery devices and prevented from being attached to other drug delivery devices.

Where the drug delivery device 50 comprises a dose setter 84, a dose of the drug delivery device 50 may be set using the dose setter 84 in a normal manner known in the art (e.g., by dialing out the appropriate number of units). The single dose setter may be operably connected to the cartridge within the cartridge holder containing a first medicament. Actuation and subsequent dispense of the medicaments may then be achieved by subcutaneously inserting the needle and activating a dose button 90 on device 50. The dose button 90 may be any triggering mechanism that causes the dose of the first medicament that was set by the dose setter to move distally towards the distal end of the device by such means as a spring, compressed gas or electrical energy.

A medicated module arrangement, for use with a drug delivery device such as the pen drug delivery device illustrated in FIG. 2, containing such a fixed dose of a second medicament may be beneficial for a number of reasons. As just one example, such a medicated module arrangement may help reduce the amount of medicament that is wasted or an amount that is "not-injected": remaining medicament left within the medicated module following an injection. (Is this better?)

Figure 3:
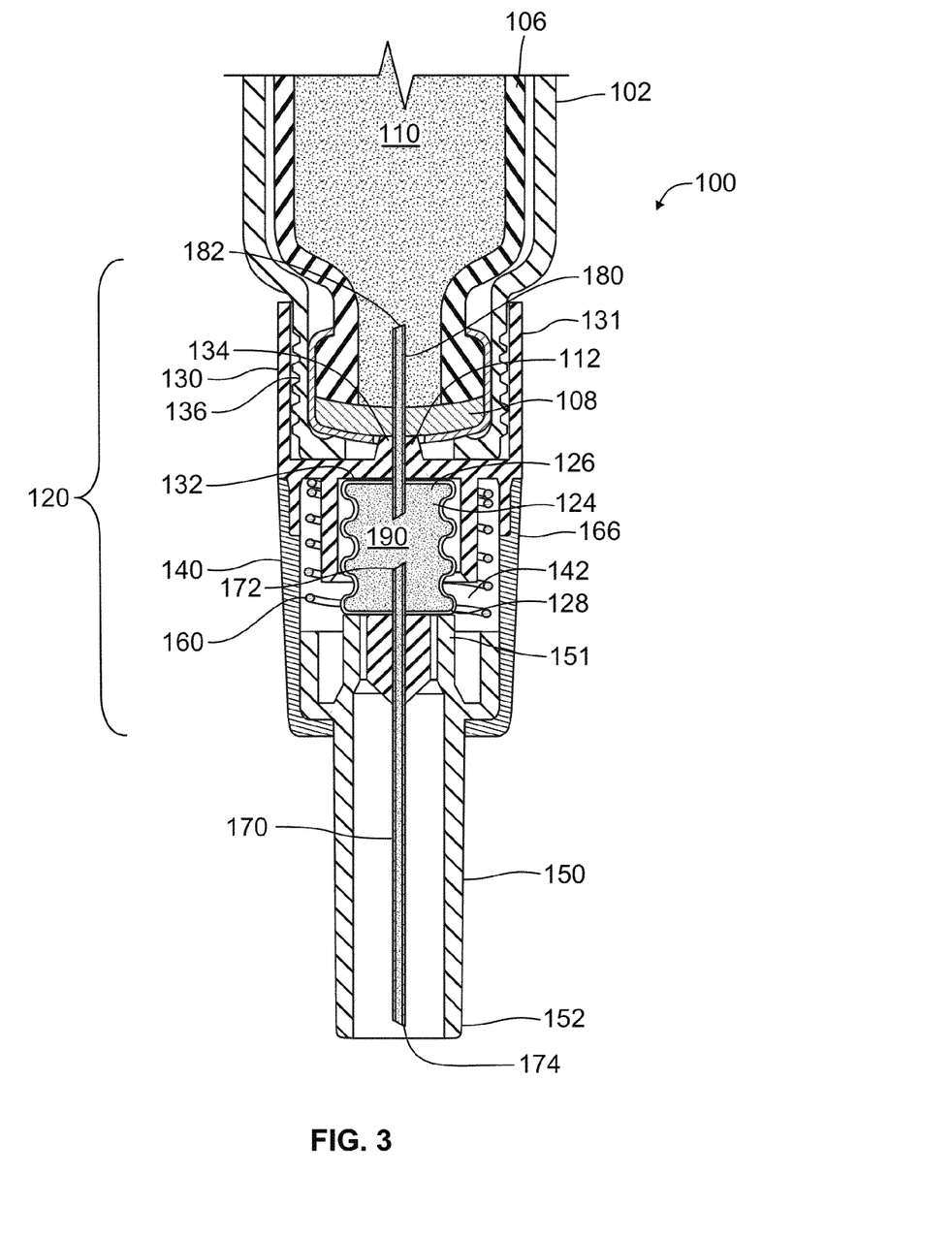
FIG. 3 illustrates a sectional view of one arrangement of a medicated module attached to a drug delivery device, such as the drug delivery device illustrated in FIG. 2.

FIG. 3 illustrates a preferred arrangement of a medicated module 100 that may be used to administer Applicants' "fixed dose, user variable dose" profile 10 illustrated in FIG. 1. As will be explained in greater detail below, in this arrangement, the medicated module 100 provides for a first medicament and a second medicament to be delivered, where one medicament is generally administered before the other medicament is administered (i.e., there is the likelihood that some mixing of the two medicaments may occur during the dose administration step). In other words, the medicated module 100 allows a fixed dose of a second medicament contained within the medicated module 100 to be substantially injected prior to injecting a variable dose of a first medicament contained within the drug delivery device.

As shown in FIG. 3, the medicated module 100 is illustrated as being attached to a drug delivery device 102. Only a portion of drug delivery device 102 is illustrated in FIG. 3. However, such a drug delivery device 102 may comprise an injection device such as the pen type injection device 50 illustrated in FIG. 2 and as described above. Preferably, the drug delivery device 102 of FIG. 3 contains a device cartridge 106 and this cartridge contains multiple doses of a first medicament 110, such as insulin.

Medicated module 100 includes an outer housing 120 wherein this housing may comprise an upper or proximal retention cap 130. This upper cap 130 may be coupled to a lower or a distal retention cap 140. Alternatively, the medicated module 100 may comprise a unitary housing. As illustrated, a proximal end 131 of the upper retention cap 130 has a connector 136 that is configured for releasable attachment to the distal end of the drug delivery device 102. This connector 136 may comprise an exclusive connector such that the upper retention cap 130 may be configured to be attached to only certain types of drug delivery devices. Alternatively, this connector 136 may comprise any type of connector generally known in the art.

Preferably, the upper retention cap 130 along with the lower retention cap 140 defines a cavity and this cavity contains a reservoir 124. This reservoir is positioned between a first and a second needle 170, 180. Most preferably, this reservoir 124 comprises a collapsible reservoir and contains a second medicament 190. In one preferred arrangement, this collapsible member 124 comprises a single dose of the second medicament 190 such as a single dose of an active agent such as GLP-1. Alternatively, this collapsible member 124 comprises a single dose of a premix of active agents or medicaments. In one preferred arrangement, this primary medicament comprises a different type of medicament as the medicament contained within the drug delivery device.

As mentioned, the collapsible reservoir 124 located between the first and second needles 170, 180 preferably comprises a top seal 126 and a bottom seal 128 of the reservoir. Prior to an injection of the secondary medicament 190, both the first and the second needles 170, 180 are in piercing engagement with the first and second seals.

As illustrated in the exemplary arrangement of FIG. 3, after the medicated module is attached to the drug delivery device and prior to injection, a proximal end 151 of the shroud 150 abuts a distal end of a collapsible member 128. The collapsible member preferably comprises a reservoir comprising a flexible or bi-stable composition. That is, the collapsible member could be made from such materials (but not limited to) TPE, rubber, multi layer extruded tubing (provides flexibility with drug compatibility assurance) or considering a rigid but foldable container it could be made from any range of compatible compounds/polymers which could be produced to include foldable elements such as multiple live hinges.

The medicated module 100 further includes a spring element 160. This spring element is arranged between a portion of the upper retention cap 130 and a portion of a shroud 150. As illustrated in FIG. 3, when the medicated module 100 is first attached to the drug delivery device 102, the spring element 160 resides in an extended state biasing the shroud to substantially cover the needle.

A shroud 150 is positioned near a distal end of the medicated module housing 120. Preferably, this shroud 150 is positioned along an inner surface of the lower retention cap 140 of the outer housing. Most preferably, this shroud 150 is configured to move in an axial direction (defined by arrow 196) against the biasing force of the spring element 160 when the medicated module 100 is positioned near an injection site and the needle inserted, such as an injection site of a human user. During an injection step, the spring element 160 compresses under an axially directed force created by the shroud 150 moving under the action of the user inserting/revealing the needle and reacted by surface 132 of the upper cap 130.

Preferably, the shroud 150 comprises a generally tubular shaped outer diameter so as to act as a needle shield. Acting as such a needle shield, the shroud 150 can tend to prevent an inadvertent needle stick of the distal needle 170 to the patient administering the dose or an individual assisting the individual receiving the dose. Aside from perhaps limiting the possibility of an inadvertent needle stick, the proposed shroud 150 may also tend to reduce any potential needle phobia that a patient may experience. In yet another arrangement, the shroud 150 could be configured with a locking mechanism so as to lock the shroud in an extended state after dose administration. One advantage of locking the shroud from repeated use is that a user will be prevented from reusing an expended medicated module and therefore eliminate the possibility that a user would use the expended medicated module under the assumption that he or she is receiving the predefined dose of the primary medicament stored in a new medicated module.

In one arrangement, Applicants' shroud 150 may be maintained within an inner cavity 142 wherein this inner cavity 142 is defined in part by the upper cap 130 and the lower retention cap 140. The shroud 150 may be opaque or non-opaque.

The medicated module 100 further comprises a needle arrangement 166. In one preferred arrangement, this needle arrangement 166 comprises a first output or distal needle 180 in combination with a second proximal needle 180.

The output or distal needle 170 is positioned within the shroud 150 and is fixed to a needle hub that moves axially with the shroud. Needle 170 comprises a distal piercing end 174 and a proximal piercing end 172. The proximal needle 180 is positioned within the upper retention cap 130 and also comprises a distal piercing end and a proximal piercing end 182. The second needle 180 is rigidly affixed in an upper surface of the upper retention cap 130.

As illustrated in FIG. 3, attachment of the medicated module 100 to the drug delivery device 102 causes the proximal piercing end 182 of a proximal needle 180 to penetrate the septum 108 of the cartridge 106 contained within the drug delivery device 102. Once the proximal needle 180 has passed through this septum 108, fluid communication will exist between the first medicament 110 contained in the cartridge 106 and the second medicament 190 contained within the collapsible reservoir 124. Penetration of the proximal needle 180 continues into the cartridge 106 until a cartridge lower surface 112 contacts a top surface 134 of the upper retention cap 130. A user may then set a dose of the drug delivery device 102 in the normal manner as described previously.

One advantage of such a medicated module arrangement is that the proposed medicated module 100 can be used to administer a fixed predetermined dose of a second medicament contained within the medicated module through a single needle 170. After this fixed predetermined dose is administered, the medicated module can be used to administer a variable dose of the first medicament contained within the drug delivery device and can administer this variable dose through this same needle 170. In a first preferred arrangement, the medicated module 100 has at least one additional benefit where the second medicament 190 is contained within the collapsible member 124 so as to minimize potential ullage of the second medicament 190 or wastage of the first medicament 110 after dispense When the medicated module 100 is initially mounted to the drug delivery device 102 as illustrated in FIG. 3, the proximal piercing end 182 of the proximal needle 180 pierces a membrane 108 of the cartridge 103 while the distal piercing end 172 remains in fluid communication with the second medicament 190 in the reservoir 124. As such, the first medicament 110 of the cartridge 106 is in fluid communication with the second medicament 190 contained in the reservoir 124.

As described, in a first medicated module 100 arrangement illustrated in FIG. 3, the module 100 comprises a needle arrangement 166 that comprises two separate hollow needles: the output needle 170 and engagement needle 180. However, in an alternative needle arrangement, this needle arrangement could comprise a unitary needle arrangement. This single needle remains in fluid communication with both the first and second medicaments 110, 190 while having a first piercing end in fluid communication with the drug delivery device 102. A second piercing end is configured for injection. The needle is in fluid communication with the collapsible reservoir 124 through a hole in a wall section of the needle. In such a preferred arrangement, the unitary needle may comprise a side-cored hole or holes where such a hole is located just below the top piercing member 126 of the collapsible reservoir 124. These holes or hole would facilitate the flow of medicament from the collapsible reservoir 124 on retraction of the needle shroud 150. This option is potentially easier to manufacture and assemble as the needle can be fixed to the top side of the collapsible reservoir and only needs to be slidably sealed to the bottom face of the collapsible reservoir 124 such that on retraction of the shroud the sealed reservoir slides up along the needle and expels the fixed dose.

Figure 4:
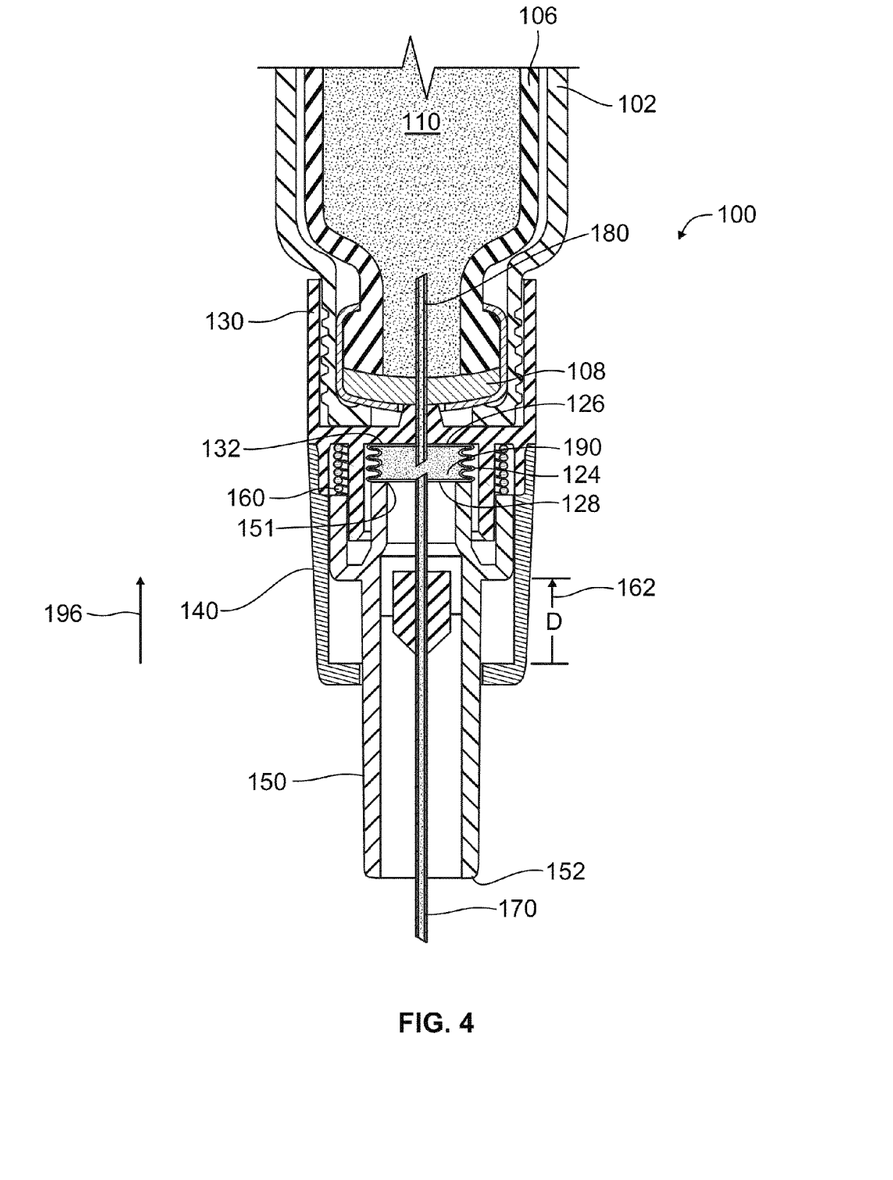
FIG. 4 illustrates a sectional view of the medicated module illustrated in FIG. 3 during a dispense step.

FIG. 4 illustrates a sectional view of the medicated module 100 during a dose administration step. During this administration step, as a user places the medicated module 100 at an injection site (e.g., on a patient's skin), the shroud 150 will move in a proximal direction (arrow 196) against the force of the biasing element 160.

During insertion of the needle by a patient, the distal end 152 of the shroud 150 contacts the injection site and shroud reacts against the injection site. As the distal needle 170 passes into the injection site, the shroud 150 is retracted back towards the upper retention cap 130, compressing the spring element 160. FIG. 4 illustrates spring element 160 in this compressed state.

After the shroud 150 has moved proximally a predetermined displacement noted in FIG. 4 by the distance D 162, the shroud 150 contacts a bottom surface 128 of the collapsible reservoir 124. Further axial displacement of the shroud 112 in the proximal direction 196 causes the collapsible reservoir 124 to compress and thereby dispense the second medicament 190 into the injection site via the distal needle 170. FIG. 4 illustrates the spring element 160 in a compressed state and the reservoir 124 in a collapsed state.

When the shroud 150 moves to its most proximal position and fully compresses the reservoir 124, the internal volume of the reservoir is minimal. This tends to minimize the ullage of the disposable fixed dose device. In an alternative arrangement, locking features may be provided on the collapsible reservoir 124 and/or the medicated module 100 or alternatively housing 120 so as to help ensure that, once compressed, the reservoir 124 cannot return to its previous un-compressed form. For example, mechanical clips or a bi-stable designed reservoir may be utilized to prevent the reservoir 124 from returning to a previous un-compressed form.

Once the distal needle 170 has been inserted to the desired depth, dosing of the first medicament (the user-selected variable dose) may then achieved via activation of the multi-use device's dispensing mechanism. For example, if the medicated module 100 were to be attached to the pen type drug delivery device of FIG. 2, the user would activate the device by pressing the dose dispense button so as to administer the previously set dose of the first medicament 110.

After setting a dose with the drug delivery device 102, if a user depresses a dosing button 142 of dose setter 140, medicament 110 from cartridge 106 is forced through the second needle 180 toward the reservoir 124, and in turn toward output needle 170. Therefore, a first dose of the fixed predetermined dose of the second medicament 190 and a potentially variable dose of the first medicament 110 is therefore substantially sequentially administered to the user through one output needle 170.

After dispense of the first medicament 110 by the user, the user may then remove the output needle 170 from the injection site. After an initial injection and after the drug delivery device and the medicated module 100 are removed from the injection site, the shroud 150 returns axially in the distal direction to an extended position. The medicated module 100 may then be removed from the drug delivery device 102 and discarded. This allows the drug delivery device 102 to be reused by the patient as required. In one alternative arrangement, features may be provided on the medicated module 100 so as to alert the user if they try to use a previously used medicated module. By virtue of the shroud 150, this particular embodiment is particularly suited towards providing features that prevent re-insertion of the needle into the skin (i.e., physically preventing the shroud from being retracted more than once). Other means of preventing reinsertion could include, but not limited to, a mechanism that allows the medicated module to be attached to a device, but once taken off not able to be reattached at all, by nature preventing re-use as it cannot be attached to the delivery device.

In an alternative medicated module arrangement, a piston arrangement may be provided in lieu of the collapsible member 124. For example, in such an arrangement, the second medicament may be contained within a cavity formed between the upper retention cap 130 and the piston, which maintains a fluid tight seal. Displacement of the shroud 150 relative to the upper retention cap 130, as described above, would cause the piston to displace the second medicament into the output needle 170 where it is dispensed. Dispense of the first medicament may then be achieved via activation of the drug delivery device as previously described.

Locking the shroud 150 in the distal position as previously mentioned is equally applicable to the piston arrangement and may provide a number of beneficial features. First, it prevents a user from re-using a non-sterile medicated module 100 after a dose has been delivered. Second, the locked shroud 150 protects and substantially conceals the injection needle 170 and therefore reduces the risk of a potential inadvertent needle stick. In addition, by substantially concealing this needle, the locked shroud 150 acts to reduce any potential needle fear, needle phobia or needle anxiety that a patient may experience. Further, such a locked shroud prevents someone from using the device a second time thinking that they are receiving a fixed dose of the secondary medicament when in fact they are not (as it was dispensed on a previous occasion).

Figure 5:
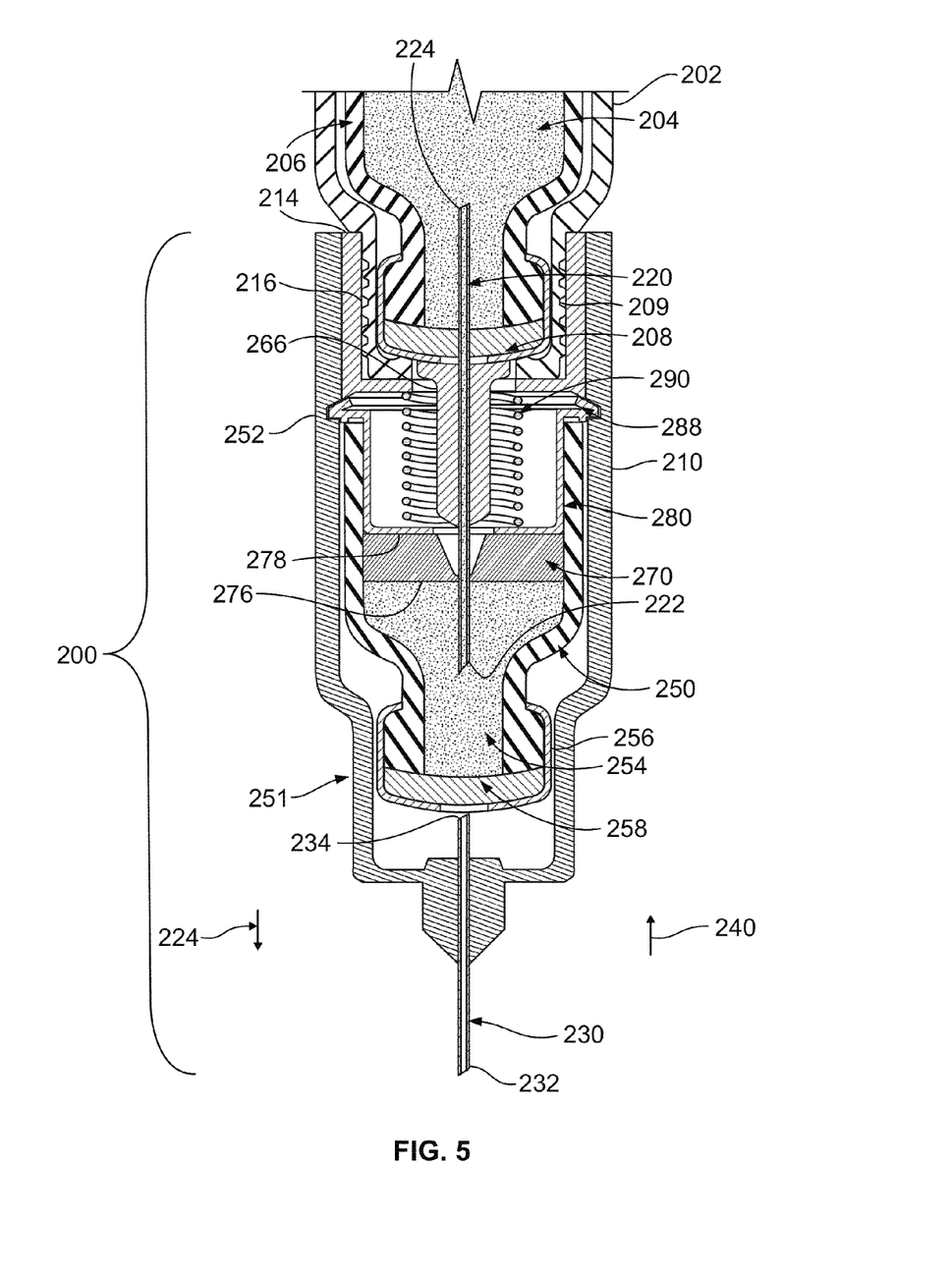
FIG. 5 illustrates a sectional view of another arrangement of a medicated module attached to a drug delivery device, such as the drug delivery device illustrated in FIG. 2.

An alternative medicated module arrangement 200 for achieving the therapeutic profile 10 illustrated in FIG. 1 is illustrated in FIG. 5. In this arrangement, the medicated module 200 comprises a small sized cartridge or reservoir 250 (e.g., a mini-cartridge). This cartridge 250 contains a second medicament 254 and a floating piston 270. A release clip 280 acts upon a preloaded spring element 290 and a proximal end portion of the cartridge so as to dispense the first and second medicaments 204, 254 through the single output needle 230. A preferred arrangement of such a medicated module 200 is described in greater below with reference to Applicants' FIGS. 5 and 6.

Figure 6:
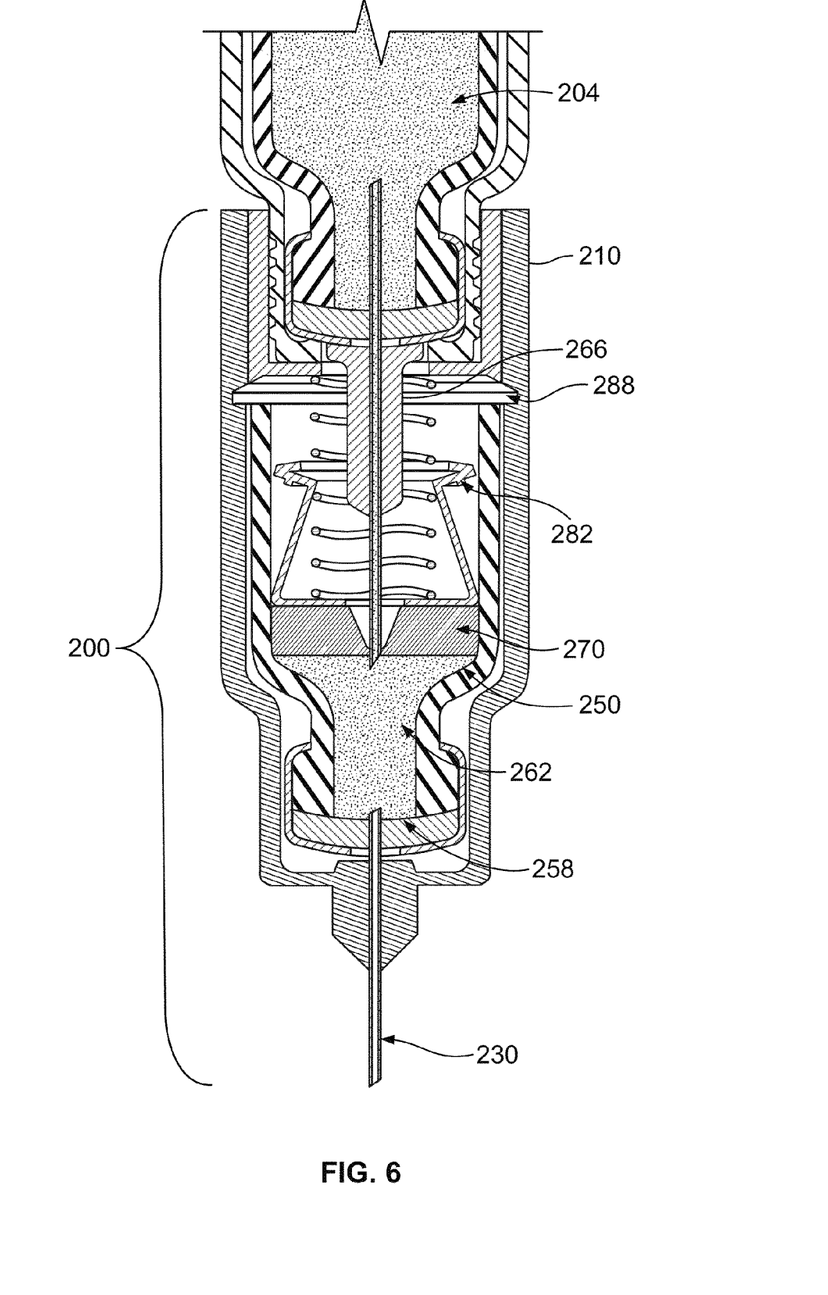
FIG. 6 illustrates a sectional view of the medicated module of FIG. 5 during a dose injection step.

As shown in FIGS. 5 and 6, the medicated module 200 is illustrated as being attached to a drug delivery device 202. Similar to the medicated module arrangement illustrated in FIG. 3, only a portion of drug delivery device 202 is illustrated in FIG. 5. As explained above, such a drug delivery device 202 may comprise an injection device such as the pen type injection device 50 illustrated in FIG. 2 and as described above.

Preferably, medicated module 200 comprises an outer housing 210 and an inner connecting portion 214. The inner connecting portion 214 is provided near the proximal end of the outer housing 210. A proximal needle 220 is contained within the outer housing 210. The outer housing further comprises a biasing member 290, a release clip 280, and a small or mini-cartridge 250 that moves during an injection step. The mini-cartridge 250 preferably contains a fixed dose of a second medicament 254, such as an active agent such as a GLP-1 or GLP-1 analog. Alternatively, this second medicament 254 may comprise a pre-mix of compounds.

This connecting member 214 is removably coupled to a distal end of a drug delivery device 202. In this preferred arrangement, the connecting member 214 comprises a threaded connection 216 that can be removably connected to a corresponding thread 209 provided along the distal portion of the drug delivery device 202. The connecting member 214 further comprises an internal needle hub 266. A proximal needle 220 is fixedly attached within this needle hub 266. Preferably, this proximal needle 220 comprises a double ended needle having a first piercing end 224 and a second piercing end 222. This first piercing end 224 is in fluid communication with the first medicament 204 contained within the drug delivery device 202.

The outer housing 210 further defines an inner surface. Near the proximal end of the outer housing 210, this inner surface defines a retention feature 288. As illustrated in FIG. 5, this retention feature 288 is geometrically configured to cooperate with a radially outwardly directed member 282 of a release clip 280. This retention feature 288 retains the release clip 280 prior to a dose injection step.

The outer housing further houses the mini-cartridge 250. This cartridge 250 comprises a floating piston 270 located near a proximal end of the cartridge 250. The floating piston 270 maintains a fluid tight seal of the second medicament 254 to the fixed dose cartridge.

The release clip 280 is provided within the outer housing 210 and is arranged to maintain an initial position of the cartridge 250 as illustrated in FIG. 5. This release clip 280, which can move axially along with the floating piston 270, engages the retention feature 288 defined along the inner surface of the outer housing 210. As illustrated, the release clip 280 is acted upon by a preloaded spring element 290. Engagement of the release clip 280 with the retention feature 288 prevents the preloaded spring element 290 from displacing the floating piston 270 or displacing the cartridge 250 within the outer housing 210.

Attachment of the medicated module 200 to the drug delivery device 202 causes the first piercing end 224 of the proximal needle 220 to penetrate the septum 208 of the cartridge 206 of the drug delivery device 202 as illustrated in FIG. 5. Once the piercing end 224 of the proximal needle 220 passes through this septum 208, fluid communication is established between the first medicament 204 contained within the cartridge 206 and the second medicament 254 contained within the cartridge 250 of the medicated module 200.

After the medicated module 200 has been attached to the drug delivery device 202, a dose from the drug delivery device can then set in the normal manner (e.g., by dialling out the appropriate number of units). Dispense of the two medicaments may then achieved via activation of the drug delivery device's dispensing mechanism wherein this dispensing mechanism causes the variable set dose of the first medicament 204 to first flow through the proximal needle 220. The first medicament 204 then flows into the cartridge 250 in the medicated module 200. As this cartridge 250 is substantially rigid and the second medicament 254 contained within the cartridge 250 is effectively incompressible, the floating piston 270 is displaced in the proximal direction shown by arrow 240. The first medicament 204 is thereby dispensed into the fixed dose cartridge 250.

At a predetermined proximal displacement of the floating piston 270 (defined by the volume of the first medicament 204 dispensed from the drug delivery device—this may also be used to control the operating limits of the medicated module—i.e., until a minimum volume of the first medicament is dispensed into the medicated module, the system will not allow dose administration), the release clip 280 which abuts a proximal surface 278 of the floating piston 270, disengages the retention feature 288. Disengagement is facilitated by the retention feature 288 being naturally biased in an inward direction.

Disengagement of the retention feature from the outer housing 210 allows the preloaded spring element 290 to displace the cartridge 250 in a distal direction (arrow 224). Distal movement of the fixed dose cartridge 250 causes a proximal end 234 of the injection needle 230 to pierce the septum 258 of the fixed dose cartridge 250. Once this septum 258 has been pierced by the injection needle 230, fluid communication is established between the cartridge 250 and the injection needle 230. The cartridge 250 moves distally until its distal most surface contacts a distal surface of the housing 210. This position of the cartridge 250 is illustrated in FIG. 6. The medicated module 200 is now ready to administer a dose of medicament.

Once fluid communication is established between the cartridge 250 and the output needle 230, the disengagement of the retention device from the end face of the fixed dose cartridge 250 causes the spring element 290 to displace the floating piston 270 in the distal direction (arrow 224). Distal movement of the piston 270 causes the mixture of the first medicament 204 and second medicament 254 contained within the fixed dose cartridge 250 to be injected into a patient injection site. Further dispense of the variable dose first medicament 204 as part of the injection stroke occurs through the reduced volume cavity formed by the cartridge 250 and floating piston 270.

At the end of the floating piston's 270 movement, the sealed volume of the cartridge 250 is minimized. This tends to minimize the ullage present in the medicated module 200 when this module is eventually discarded. In one preferred arrangement, a distal end 276 of the floating piston 270 may be profiled to closely match an inner profile of distal end of the mini-cartridge 250 to help further minimize any ullage remaining in the module 200 after drug dispense.

After complete dispense of the first medicament 204, the distal needle 230 can be removed from the injection site and the medicated module 200 may be discarded, allowing the drug delivery device to be reused as required.

The medicated module arrangements herein disclosed are preferably self-contained and may be provided as a sealed and sterile disposable module. Such a module may comprise an attachment means, such as a threaded connector, compatible to the attachment means at the distal end of the drug delivery device. Although not shown, the medicated modules disclosed herein could be supplied by a manufacturer contained in a protective and sterile capsule or container where the user would peel or rip open a seal or the container itself to gain access to the sterile medicated module. In some instances it might be desirable to provide two or more seals for each end of the medicated module.

Moreover, in the arrangements discussed above, these arrangements have the benefit in that the second medicament is contained entirely within the medicated module, separate and away from the first medicament contained within the drug delivery device.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module for use with a drug delivery device, said medicated module comprising:
    a housing configured for attachment to said drug delivery device, said drug delivery device comprising a first medicament;
    a collapsible reservoir contained within said housing;
    a pre-determined volume of a second medicament contained within said collapsible reservoir;
    a needle arrangement configured within said housing, said needle arrangement arranged in fluid communication with said collapsible reservoir and said drug delivery device; and
    a needle shroud configured partially within said housing;
    wherein, said needle shroud is configured to compress said collapsible reservoir to dispense said second medicament through said needle arrangement.

2. The medicated module of claim 1, wherein, during dispense, said second medicament is dispensed before a first dose of said first medicament contained within said drug delivery device.

3. The medicated module of claim 2, wherein said first dose of said first medicament contained within said drug delivery device comprises a fixed dose.

4. The medicated module of claim 2, wherein said first dose of said first medicament comprises a variable dose.

5. The medicated module of claim 1, wherein said pre-determined volume of said second medicament contained within said collapsible reservoir comprises a fixed dose of said second medicament.

6. The medicated module of claim 1, wherein said housing is configured for permanent attachment to said drug delivery device.

7. The medicated module of claim 1, wherein said shroud is biased within said housing.

8. The medicated module of claim 7, wherein said shroud is biased within said housing by a spring.

9. The medicated module of claim 1, wherein a portion of said shroud comprises a tubular shape so that said tubular shape substantially conceals a portion of said needle arrangement.

10. The medicated module of claim 1, wherein said needle arrangement comprises
    a first needle in fluid communication with said collapsible reservoir, and
    a second needle in fluid communication with both said first medicament contained within said drug delivery device and said collapsible reservoir.

11. The medicated module of claim 1, wherein said needle arrangement comprises a single unitary needle configured to be in fluid communication with both the first and second medicaments; wherein said single unitary needle comprises (i) a proximal piercing end configured for fluid communication with the drug delivery device; (ii) a distal piercing end configured for injection; (iii) and at least one side-cored hole located inside said collapsible reservoir; wherein the at least one hole is arranged to facilitate the flow of medicament from the collapsible reservoir on retraction of the needle shroud.

12. The medicated module of claim 11 wherein, the at least one side-cored hole is located just below the top piercing member of the collapsible reservoir.

13. The medicated module of claim 11 wherein, on retraction of the shroud the sealed reservoir slides up along the needle and the medicament is expelled.

14. The medicated module of claim 1, wherein said second medicament comprises a GLP-1 or GLP-1 analog.

15. The medicated module of claim 1, wherein said drug delivery device comprises a pen injector.

* * * * *